United States Patent [19]

Macklin

[11] Patent Number: 5,662,678

[45] Date of Patent: Sep. 2, 1997

[54] SELF INJECTION ARM CLAMP

[76] Inventor: John W. Macklin, S1110 10531 90 St., Edmonton, Alberta, Canada, T5H 4E7

[21] Appl. No.: 724,329

[22] Filed: Oct. 11, 1996

[51] Int. Cl.⁶ .................................................. A61B 17/00
[52] U.S. Cl. ........................................... 606/201; 606/202
[58] Field of Search .................................... 606/201, 202, 606/203, 204; 602/53, 58

[56]  References Cited

U.S. PATENT DOCUMENTS

| 4,195,636 | 4/1980 | Behnke | 606/201 |
| 4,662,356 | 5/1987 | Aronsohn | 606/201 |

*Primary Examiner*—Michael Buiz
*Assistant Examiner*—Kevin Truong
*Attorney, Agent, or Firm*—G. F. Gallinger

[57] ABSTRACT

An injection clamp for lifting and holding skin on an upper arm comprising: a pair of mating parallel elongated jaw members; a pair of mating arm members hinged together at one end, each arm member having a hinge end portion which carries an elongate jaw member extending laterally therefrom, each arm member having a rounded central portion adapted to extend around one side of the upper arm, and a spring end portion, said spring end portion being the end of the arm member opposite the hinge end; and, tension spring extending between the spring end portions of the pair of mating arm members is disclosed. The unique design of the clamp allows one to single handedly slide the clamp over the upper arm, open the spring end portion thereof with one's fingers, and then while pulling the elongate jaw members towards the arm—allow the spring end portion to close so that the skin is pinched between the elongate jaw members. The mechanical leverage inherent in the design results in a much smaller force being required to open the arm members than is exerted between the jaw members. The squeezed skin is wholly exposed and unobstructed by the clamp for injection.

11 Claims, 1 Drawing Sheet

SELF INJECTION ARM CLAMP

FIELD OF THE INVENTION

This invention relates to devices used to lift and hold the skin on the upper arm for subcutaneous self injection.

BACKGROUND OF THE INVENTION

Many individuals suffering from allergies require monthly subcutaneous injections. Many diabetics similarly require daily subcutaneous injections. It is much quicker, convenient and economical for an individual requiring regular subcutaneous injections to self administer them rather than fit their routine into another's schedule. However, to pinch the upper arm, a preferred injection area, with one hand and to inject with the other is not physically possible.

Accordingly, many styles of clamps have been designed to pinch and hold the upper arm skin in a lifted position so that the hand on the opposite arm is left free to manipulate a syringe for subcutaneous injection of the exposed, lifted skin.

The problem with most of the clamps available is that they either pinch the skin too hard or insufficiently. It is difficult to regulate the force which the clamp applies on the pinched skin, and it is even more difficult to maintain that force over an extended period when the clamp must be opened wide to slip over the elbow and accept the lifted skin. Another problem with most of the clamps available is that they are difficult to hold open and manipulate into position with a single hand.

OBJECTS AND STATEMENT OF THE INVENTION

It is an object of this invention to disclose a self injection upper arm clamp which is easily held open yet which squeezes the skin sufficiently due to a design which incorporates mechanical leverage. It is an object of this invention to disclose a clamp which applies a regulated force to the pinched skin. It is yet a further object of this invention to disclose a self injection upper arm clamp which will maintain the force with which it pinches over time when it is regularly opened to an extended position. It is yet a further object of this invention to disclose a clamp which is relatively easily held open and manipulated into position by a single hand. It is yet a final object of this invention to disclose a clamp which can accommodate widely varying upper arm sizes at multiple positions therealong.

One aspect of this invention provides for an injection clamp for lifting and holding skin on an upper arm comprising: a pair of mating parallel elongated jaw members; a pair of mating arm members hinged together at one end, each arm member having a hinge end portion which carries an elongate jaw member extending laterally therefrom, each arm member having a rounded central portion adapted to extend around one side of the upper arm, and a spring end portion, said spring end portion being the end of the arm member opposite the hinge end; and, tension means extending between the spring end portions of the pair of mating arm members.

A preferred aspect of this invention provides for a clamp as above wherein the hinge end portion of each lateral arm member is provided with an elongated lateral hole adapted to receive and carry the elongate Jaw member which laterally extends therefrom and the elongate jaw members are held to the arm members by a screw so that the spacing between the elongate jaw members may be adjusted.

Various other objects, advantages and features of novelty which characterize this invention, are pointed out with particularity in the claims annexed to, and forming part of this disclosure. For a better understanding of the invention, its operating advantages, and the specific objects attained by its users, reference should be made to the accompanying drawings and description, in which preferred embodiments of the invention are illustrated.

FIGURES OF THE INVENTION

The invention will be better understood and objects other than those set forth will become apparent to those skilled in the art when consideration is given to the following detail. description thereof. Such description make reference to the annexed drawings wherein:

FIG. 4 shows an alternative design to that shown in FIG. 3 wherein each arm member has an equal offset.

Figure 1:
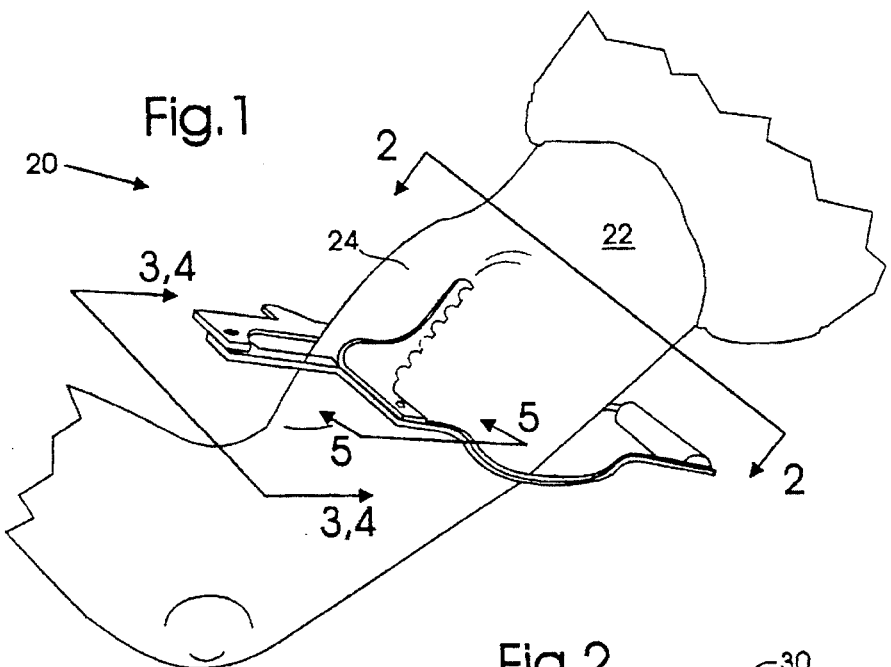
FIG. 1 is a perspective view of a self injection arm clamp positioned on an upper arm lifting and holding the skin.

The following is a discussion and description of the preferred specific embodiments of this invention, such being made with reference to the drawings, wherein the same reference numerals are used to indicate the same or similar parts and/or structure. It should be noted that such discussion and description is not meant to unduly limit the scope of the invention.

DESCRIPTION OF THE INVENTION

Figure 2:
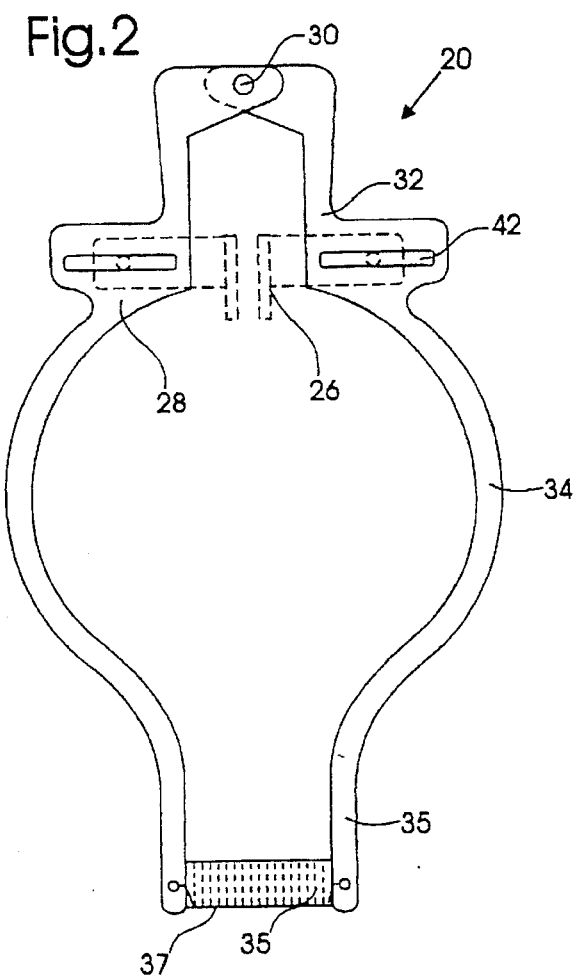
FIG. 2 is a front view of the clamp as viewed from line 2—2 on FIG. 1 having the elongate jaws thereon shown in ghost.

Turning now to the drawings and more particularly to FIG. 1 we have a perspective view of a Self Injection Arm Clamp 20 positioned on an upper arm 22 lifting and holding the skin 24. FIG. 2 is a front view of the clamp 20 as viewed from line 2—2 on FIG. 1 having the elongate jaw members 26 thereon shown in ghost. The injection clamp 20 for lifting and holding skin 24 on an upper arm 22 comprises: a pair of mating parallel elongated jaw members 26; a pair of generally planar mating arm members 28 hinged 30 together at one end, each arm member 28 having a hinge end portion 32 which carries an elongate jaw member 26 extending laterally therefrom, each arm member 28 having a rounded central portion 34 adapted to extend around one side of the upper arm 22, and a spring end portion 36, said spring end portion 36 being the end of the arm member 28 opposite the hinge end portion 32; and, tension means, which is preferably a helical spring 35 extending between the spring end portions 36 of the pair of mating arm members 28. The spring end portion 36 comprises a straight elongate portion having an inner end carried by the central portion 34 and an outer end to which one end of the helical spring 35 is connected. A spring cover 37 is provided.

Figure 3:
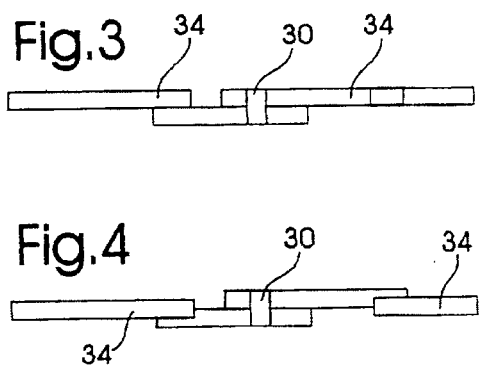
FIG. 3 is an end view taken along line 3—3 on FIG. 1 wherein only one arm member is offset.
Figure 4:
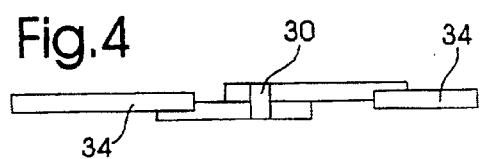
FIG. 4 is an end view taken along line 4—4 on FIG. 1.

The hinge end portion 32 of at least one arm member 28 is offset so that the arm members 28 g y move in the same plane. FIG. 3 is an end view taken line 3—3 on FIG. 1 wherein only one arm member 28 is offset. FIG. 4 shows an alternative design to that shown in FIG. 3 wherein both arm members 28 are offset an equal amount so that the mating arm members 28 generally move in the same plane. In the preferred embodiment the arm members 28 and the jaw members 26 are fabricated from a metal plate.

Figure 5:
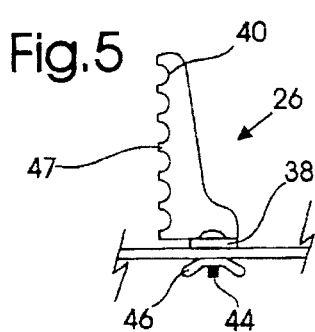
FIG. 5 is a front view of an elongate jaw taken along line 5—5 on FIG. 1.

FIG. 5 is a front view of an elongate jaw member 26 taken along line 5—5 on FIG. 1. The elongate jaw member 26 has mounting base 38 and a perpendicular elongate jaw portion 40. FIG. 3 shows the hinge end portion 32 of each lateral arm member 28 being provided with an elongated lateral hole 42 adapted to receive and carry the elongate jaw member 26 which laterally extends therefrom. The mounting base 38 of the elongate jaw member 26 is held thereto by a screw 44 which is provided with a wing nut 46, so that the spacing between the elongate jaw portions 40 may be adjusted. The base 46 of the elongate jaw portion is roughened to better hold the skin 24 on the upper arm 22.

The unique design of the self injection arm clamp 20 allows one to single handedly slide the clamp 20 over the upper arm 22, open the spring end portion 36 thereof with one's fingers, and then while pulling the elongate jaw members 26 towards the arm—allow the spring end portion to close so that the skin 24 is pinched between the elongate jaw members 26. The mechanical leverage inherent in the design results in a much smaller force being required to open the arm members 28 than is exerted between the jaw members 26. The squeezed skin 22 is wholly exposed and unobstructed by the clamp 20 for injection. The elongate holes 42 in the arm members allow one to adjust the spacing of the elongate jaw members 26 when they are in the closed position, thereby ensuring comfort by allowing adjustment for differing skin thicknesses caused by differing skin caused by differing thicknesses of subcutaneous fat.

While the invention has been described with preferred specific embodiments thereof, it will be understood that this description is intended to illustrate and not to limit the scope of the invention. The optimal dimensional relationships for all parts of the invention are to include all variations in size, materials, shape, form, function, assembly, and operation, which are deemed readily apparent and obvious to one skilled in the art. All equivalent relationships to those illustrated in the drawings, and described in the specification, are intended to be encompassed in this invention. What is desired to be protected is defined by the following claims.

I claim:

1. An injection clamp for lifting and holding skin on an upper arm comprising:
   a pair of mating parallel elongated jaw members;
   a pair of mating arm members hinged together at one end, each arm member having a hinge end portion which carries one of the elongated jaw members extending laterally therefrom, each arm member having a rounded central portion adapted to extend around one side of the upper arm, and a spring end portion, said spring end portion being the end of the arm member opposite the hinge end; and,
   tension means extending between the spring end portions of the pair of mating arm members.

2. A clamp as in claim 1 wherein the tension means is a helical spring.

3. A clamp as in claim 2 wherein the spring end portion comprises a straight elongate portion having an inner end carried by the central portion and an outer end to which one end of the helical spring is connected.

4. A clamp as in claim 3 wherein the mating arm members are generally planar.

5. A clamp as in claim 4 wherein the hinge end portion of one arm member is offset so that the mating arm members generally move in the same plane.

6. A clamp as in claim 4 wherein the hinge end portions of both arm members are offset an equal amount so that the mating arm members generally move in the same plane.

7. A clamp as in claim 4 wherein the hinge end portion of each arm member is provided with a lateral hole adapted to receive and carry the elongate jaw member which laterally extends therefrom.

8. A clamp as in claim 7 wherein the lateral hole is elongated and the elongate jaw members are held to the arm members by a screw so that the spacing between the elongate jaw members may be adjusted.

9. A clamp as in claim 8 wherein the elongate jaw member has a mounting base and a perpendicular elongate jaw portion.

10. A clamp as in claim 7 wherein the arm members and the jaw members are fabricated from a metal plate.

11. A clamp as in claim 10 further comprising a spring cover.

* * * * *